US00RE37908E

(19) United States
(12) Reissued Patent
Kinsey

(10) Patent Number: US RE37,908 E
(45) Date of Reissued Patent: Nov. 19, 2002

(54) NEEDLE HOLDER FOR FLUID COLLECTION AND/OR INJECTION SYSTEM

(75) Inventor: Phillip Spencer Kinsey, Newington, CT (US)

(73) Assignee: Bio-Plexus, Inc., Vernon, CT (US)

(21) Appl. No.: 09/579,315

(22) Filed: May 25, 2000

Related U.S. Patent Documents

Reissue of:
(64) Patent No.: 5,755,673
Issued: May 26, 1998
Appl. No.: 08/904,811
Filed: Aug. 1, 1997

U.S. Applications:
( 63) Continuation of application No. 08/580,322, filed on Dec. 28, 1995, now abandoned.

(51) Int. Cl.[7] ..... A61B 5/00
(52) U.S. Cl. ..... 600/577
(58) Field of Search ..... 600/573, 576–578; 604/187, 192

(56) References Cited

U.S. PATENT DOCUMENTS

| | | | | | |
|---|---|---|---|---|---|
| 1,231,497 | A | * | 6/1917 | Cook | |
| RE16,836 | E | * | 10/1927 | Cook | |
| 1,667,454 | A | * | 4/1928 | Brix | |
| 1,757,680 | A | * | 2/1930 | Neil | |
| 2,376,436 | A | * | 1/1945 | Lawshe | |
| 2,392,196 | A | * | 1/1946 | Smith | |
| 3,159,159 | A | * | 12/1964 | Cohen | |
| 3,706,306 | A | * | 12/1972 | Berger et al. | |
| 3,974,832 | A | * | 8/1976 | Kruck | 128/221 |
| 4,150,666 | A | * | 4/1979 | Brush | 128/2 F |
| 4,154,229 | A | * | 5/1979 | Nugent | 128/764 |
| 4,155,350 | A | * | 5/1979 | Percarpio | 128/764 |
| 4,333,478 | A | * | 6/1982 | Krieg | 128/764 |
| 4,409,990 | A | * | 10/1983 | Mileikowsky | 128/763 |
| 4,731,059 | A | * | 3/1988 | Wanderer et al. | 604/192 |
| 4,740,205 | A | * | 4/1988 | Seltzer et al. | 604/192 |
| 4,788,986 | A | * | 12/1988 | Harris | 128/763 |
| 4,802,579 | A | * | 2/1989 | Hall et al. | 206/366 |
| 4,822,343 | A | * | 4/1989 | Beiser | 604/187 |
| 4,840,619 | A | * | 6/1989 | Hughes | 604/187 |
| 4,841,985 | A | * | 6/1989 | Wanamaker | 128/763 |
| 4,904,244 | A | * | 2/1990 | Harsh et al. | 604/187 |
| 4,907,600 | A | * | 3/1990 | Spencer | 128/764 |
| 4,942,881 | A | * | 7/1990 | Al-Sioufi et al. | 128/763 |
| 4,974,603 | A | * | 12/1990 | Jacobs | 128/763 |
| 4,984,580 | A | * | 1/1991 | Wanamaker | 128/763 |
| 4,993,426 | A | * | 2/1991 | Spencer | 128/763 |
| 5,062,837 | A | * | 11/1991 | Al-Sioufi et al. | 604/240 |
| 5,069,225 | A | * | 12/1991 | Okamura | 128/765 |
| 5,117,837 | A | * | 6/1992 | Wanamaker et al. | 128/763 |
| 5,120,311 | A | * | 6/1992 | Sagstetter et al. | 604/110 |
| 5,143,083 | A | * | 9/1992 | Al-Sioufi et al. | 128/763 |
| 5,219,333 | A | * | 6/1993 | Sagstetter et al. | 604/110 |
| 5,299,687 | A | * | 4/1994 | Hanifl et al. | 206/370 |
| 5,476,106 | A | * | 12/1995 | Gartz | 128/898 |

FOREIGN PATENT DOCUMENTS

| | | | |
|---|---|---|---|
| DE | 883053 | * | 7/1953 |
| DE | 2147183 | * | 7/1975 |
| DE | 3049503 | * | 4/1983 |
| FR | 2564726 | * | 11/1985 |
| GB | 802351 | * | 10/1958 |
| RU | 801838 | * | 2/1981 |
| WO | WO 89/05118 | * | 6/1989 |

* cited by examiner

*Primary Examiner*—Max Hindenburg
(74) *Attorney, Agent, or Firm*—Libert & Associates; Victor E. Libert

(57) ABSTRACT

A needle holder for use with a fluid transfer system of the type having a standard threaded cannula and a fluid container. The needle holder includes an actuation mechanism for detachably mounting a cannula to the holder, the actuation mechanism including pivotable threaded halves and an actuator operably associated therewith. In a cannula-mounting position, facing surfaces on the threaded halves cooperate to define a threaded passageway for engaging the cannula. Upon operation of the actuator, the threaded halves pivot to a retracted position to disengage from the cannula.

32 Claims, 4 Drawing Sheets

NEEDLE HOLDER FOR FLUID COLLECTION AND/OR INJECTION SYSTEM

Matter enclosed in heavy brackets [ ] appears in the original patent but forms no part of this reissue specification; matter printed in italics indicates the additions made by reissue.

This application is a continuation of application Ser. No. 08/580,322 filed on Dec. 28, 1995, now abandoned.

BACKGROUND OF THE INVENTION

1. Field of the Invention

The present invention relates to the manipulation of devices through which fluids are delivered to and/or withdrawn from an animal through venipuncture. More particularly, this invention is directed to a holder for use with a fluid collection and/or injection system of the type including a double ended needle assembly and associated fluid container and, specifically, to such a holder having an actuation mechanism for selectively mounting or detaching the needle assembly. Accordingly, the general objects of the present invention are to provide novel and improved methods and apparatus of such character.

2. Description of the Related Art

While not limited thereto in its utility, the present invention is particularly well suited for use in fluid transfer systems of the type which are used to inject fluids into and to draw blood specimens from a patient. Current medical practice requires that the fluid containers and needle assemblies used in such systems be inexpensive and readily disposable. Consequently, existing blood collection systems, for example, typically employ some form of durable, reusable holder on which detachable and disposable needles and fluid collection tubes may be mounted. A blood collection system of this nature can be assembled prior to use and then disassembled after usage. Thus, these blood collection systems allow repeated use of the relatively expensive holder upon replacement of the relatively inexpensive disposable needle and/or fluid collection tube. In addition to reducing the cost of collecting blood specimens, these blood collection systems also help minimize the production of hazardous medical waste.

The most popular design configuration of previously available blood collection systems includes a double ended needle assembly, an evacuated collection tube, and a holder for maintaining the needle assembly and the collection tube in fixed relation. The double ended needle assembly, which is also referred to as a cannula, has a bore extending therethrough and a hub near a central region thereof. The evacuated fluid collection tube includes a puncturable stopper at one end thereof. In this type of blood collection system, the holder typically has a housing at one end thereof for receiving the needle assembly. Likewise, the holder also has a hollow body with an opening at an opposite end thereof for receiving the collection tube. The needle assembly is rigidly received within the housing of the holder such that a first end of the needle extends forwardly of the holder for puncturing the vein of a patient. The opposite, second end of the needle extends into the hollow body of the holder. Upon assembly of the blood collection system, the needle assembly is inserted into the housing and the collection tube is inserted through the open end of the hollow body until the second end of the needle pierces the puncturable stopper of the collection tube, thereby allowing fluid communication between the interior of the collection tube and the bore which extends through the needle assembly. To draw a blood specimen from a patient using one of these blood collection systems, the evacuated collection tube is partially inserted into one end of the holder, the first end of the needle is inserted into a patient's vein and the collection tube is fully inserted into the holder such that blood will be drawn through the bore of the needle assembly and into the fluid collection tube. After drawing the specimen, the collection tube is removed so that the blood contained therein can be analyzed and the needle assembly is detached for disposal. In addition to being capable of accommodating blood collection tubes, the holders of some prior art fluid transfer systems are compatible with fluid containers having a fluid to be injected into a patient. Thus, such holders can be used to inject fluid into, as well as draw blood specimens from, a patient. Efforts to improve prior art fluid transfer systems of the type briefly described above have largely focused on improving the mechanism for removably mounting the needle assembly to the holder.

One early, and extremely popular, type of mechanism for removably mounting a needle assembly to a holder utilized a fixed threaded passageway at one end of the holder designed to threadably receive complementary threads on the hub of the needle assembly. With a holder of this type, a threaded cannula could be screwed into position prior to drawing a blood specimen from a patient, subsequently unscrewed from the holder and discarded.

Blood collection systems employing a holder with a fixed threaded passageway, however, suffer from a number of serious deficiencies. The most serious of these deficiencies stems from the need for the health care worker to physically handle the cannula after it has been in contact with the patient's blood in order to unscrew the threaded cannula from the holder. This handling typically entails placing a protective cap on the externally extending portion of the threaded cannula, twisting the threaded cannula to free it from the fixed threaded passageway of the holder, and disposing of the used cannula. Thus, removal of the needle from a blood collection device of this type inevitably gives rise to the possibility of accidental contact between the health care worker and the patient's blood. Another deficiency of the above-described arrangement resides in the relatively long period of time it takes a health care worker to remove the needle from the holder. Nonetheless, due to widespread usage of this type of blood collection system, health care workers have now become accustomed to using threaded cannulas.

In response to the above-mentioned deficiencies of fixed threaded passageway holders, holders have recently been developed which employ unthreaded needle-locking mechanisms with a remote release element for ejecting the needle assembly from the needle-locking mechanism. This type of arrangement has generally been considered to be a functional improvement over fixed threaded passageway holders because, by operating the release element, a health care worker may quickly remove a needle assembly from a holder without the need to physically contact any portion of the needle assembly directly. This reduces the risk that the health care worker will accidentally contact the patient's blood. To date, however, most of the blood collection devices with holders having releasable needle-locking mechanisms have been incompatible with what has now become the industry standard threaded cannula, i.e., a double needle assembly with a threaded hub in a central region thereof and a hub disk located at one end of the threaded portion of the hub. Thus, most of these recently developed holders have required the use of relatively expensive, custom designed needle assemblies.

Holders having a needle ejection feature which are compatible with the standard double needle configuration have also been developed. However, these holders have either suffered from overall poor performance and/or have required the use of a separate adapter, for accommodating a standard threaded cannula, which is discarded along with the cannula upon removal of the cannula from the holder. In addition to increasing the overall cost of the blood collection system, the use of such an adapter can also unnecessarily complicate assembly and/or disassembly of the blood collection system.

In light of the foregoing, there exists a need in the health care industry for a needle holder for use with a fluid transfer system which (1) is compatible with standard threaded cannulas; (2) allows a user to detach a threaded cannula from the holder without physically handling any portion of the threaded cannula; and (3) is capable of operating effectively without the need for any additional components.

SUMMARY OF THE INVENTION

The present invention satisfies the above needs, and overcomes the above-stated and other deficiencies of the prior art, by providing a holder having a cannula actuation mechanism within a housing at one end of the holder for removably mounting an externally threaded cannula thereto. The actuation mechanism includes first and second mounting jaws, which may comprise first and second threaded halves with surfaces which cooperate to define a threaded passageway therebetween when the threaded halves are in a cannula-mounting position. At least one of the threaded halves is mounted within the housing in such a manner as to allow movement thereof from the cannula-mounting position to a retracted position wherein the threaded surfaces define a gap which is appreciably greater than the maximum cross-section of the cannula hub. The actuation mechanism also includes an actuator with at least one structural portion for normally maintaining the threaded halves in the cannula-mounting position. The actuator is slidably mounted to the holder and operably associated with the threaded halves such that, upon user-operation of the actuator, at least one of the threaded halves moves to the retracted position. To removably mount a standard double ended cannula to a holder in accordance with the present invention, a user simply inserts a standard threaded cannula, with its protective cap in place, into the holder and screws the threads of the cannula hub into the threaded passageway defined by the threaded surfaces of the threaded halves until the hub disk of the cannula hub abuts the top surfaces of the threaded halves. To release a threaded cannula from a holder in accordance with the present invention, the user simply orients the holder over a "sharps disposal box" such that the first end of the cannula extends vertically below the holder, and depresses the actuator to retract the threaded halves thereby allowing the cannula to fall from the holder under the force of gravity.

The cannula holder of the present invention is wholly compatible with standard threaded cannulas. This compatibility is achieved by pivotably mounting at least one of the threaded halves of the actuation mechanism within a housing located at one end of the holder. When these threaded halves are in the cannula-mounting position, a standard threaded cannula can be threaded into the threaded passageway in the same manner as a standard threaded needle assembly would be threaded into a holder having a fixed threaded passageway. However, upon user-operation of an actuator, which is located on the holder in a position where it is unlikely to be contaminated, at least one of the threaded halves pivots apart to a retracted position, thereby detaching the threaded cannula from the actuation mechanism. Thus, the present invention is compatible with standard threaded needle assemblies and can be used by health care workers in a manner substantially similar to the prior art needle holders to which they are accustomed.

Another significant advantage of the present invention when compared to previously available needle holders with an ejection capability is reduced cost. Since the present invention is wholly compatible with both standard threaded cannulas and standard fluid collection tubes, holders in accordance with the present invention do not require the use of expensive custom made cannulas and/or additional custom made components.

Yet another advantage of the invention relative to previously available fluid collection devices is improved reliability and ease of operation. To assemble a fluid transfer device using a holder in accordance with the present invention, a user simply threads a standard cannula into the actuation mechanism at one end of the holder and inserts a fluid container into an opening at the opposite end of the holder. After use, the fluid container is removed from the holder, the holder is positioned over a "sharps disposal box", and the actuator is depressed thereby retracting the threaded halves of the holder and allowing the cannula to fall into the "sharps disposal box" under the force of gravity. This assembly procedure is identical to the assembly procedure used with conventional prior art holders. The disassembly procedure, on the other hand, avoids the need to unscrew a cannula, twist a bayonet mechanism or flip a lever as was necessary with various prior art holders.

BRIEF DESCRIPTION OF THE DRAWINGS

The present invention will be described below with reference to the accompanying drawings, wherein like reference numerals represent like elements in the several figures, and wherein:

FIG. 4a illustrating the actuation mechanism in the cannula-mounting position; FIG. 4b illustrating the actuation mechanism in the retracted position.

DESCRIPTION OF THE DISCLOSED EMBODIMENT

Figure 1:
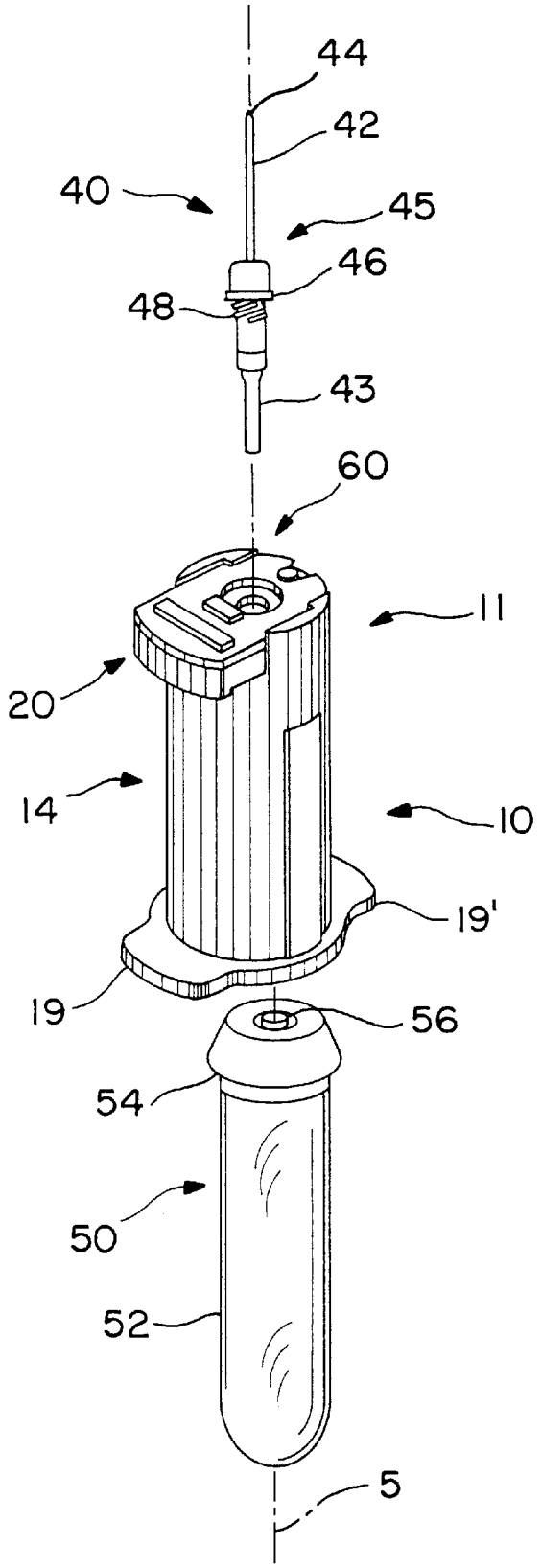
FIG. 1 is a perspective view of one embodiment of a holder in accordance with the present invention shown in combination with a standard threaded cannula and a standard fluid collection tube.

With reference to the drawings, FIG. 1 shows a perspective view of a holder 10 in accordance with the present invention in combination with a standard threaded cannula 40 and a standard collection tube 50. Holder 10 generally consists of a hollow body 14, a housing 11 having an end cap 60 at one end thereof, and an actuation mechanism 20. Body 14 of holder 10 defines a longitudinal axis 5. Threaded cannula 40 is shown in axial alignment with axis 5 for insertion into actuation mechanism 20. Threaded cannula 40 has a first end 42, a second end 43, and a threaded hub, indicated generally at 45, intermediate the ends. A longitudinal bore 44 extends along the length of cannula 40. Hub 45 of threaded cannula 40 includes a threaded portion 48 which terminates, at one end thereof, at a hub disk 46. When cannula 40 is mounted on holder 10, the first end 42 extends forwardly of holder 10 and the second end 43 extends into hollow body 14.

Collection tube 50, when the system is assembled and in use, will also be in axial alignment with hollow body 14 of holder 10 and will be received therein. Collection tube 50, in the disclosed embodiment, is a standard evacuated blood specimen collection tube which consists of an elongated tube 52 having a rubber stopper 54 at one end thereof. The rubber stopper 54 has a puncturable membrane 56 in a central region of the stopper 54. Upon insertion of collection tube 50 into the hollow region of hollow body 14, second end 43 of threaded cannula 40 pierces membrane 56 and extends into the interior of tube 52. Thus, when the fluid transfer system is fully assembled, bore 44 of cannula 40 is in fluid communication with the interior of collection tube 50 and the system can be used to draw a blood specimen from a patient. Alternatively, the present invention may be used to inject a fluid into a patient using a fluid container with a piston for injection of a fluid into a patient. First and second grip tabs 19 and 19' on holder 10 assist insertion of collection tube 50, or other fluid container, into holder 10.

Figure 2:
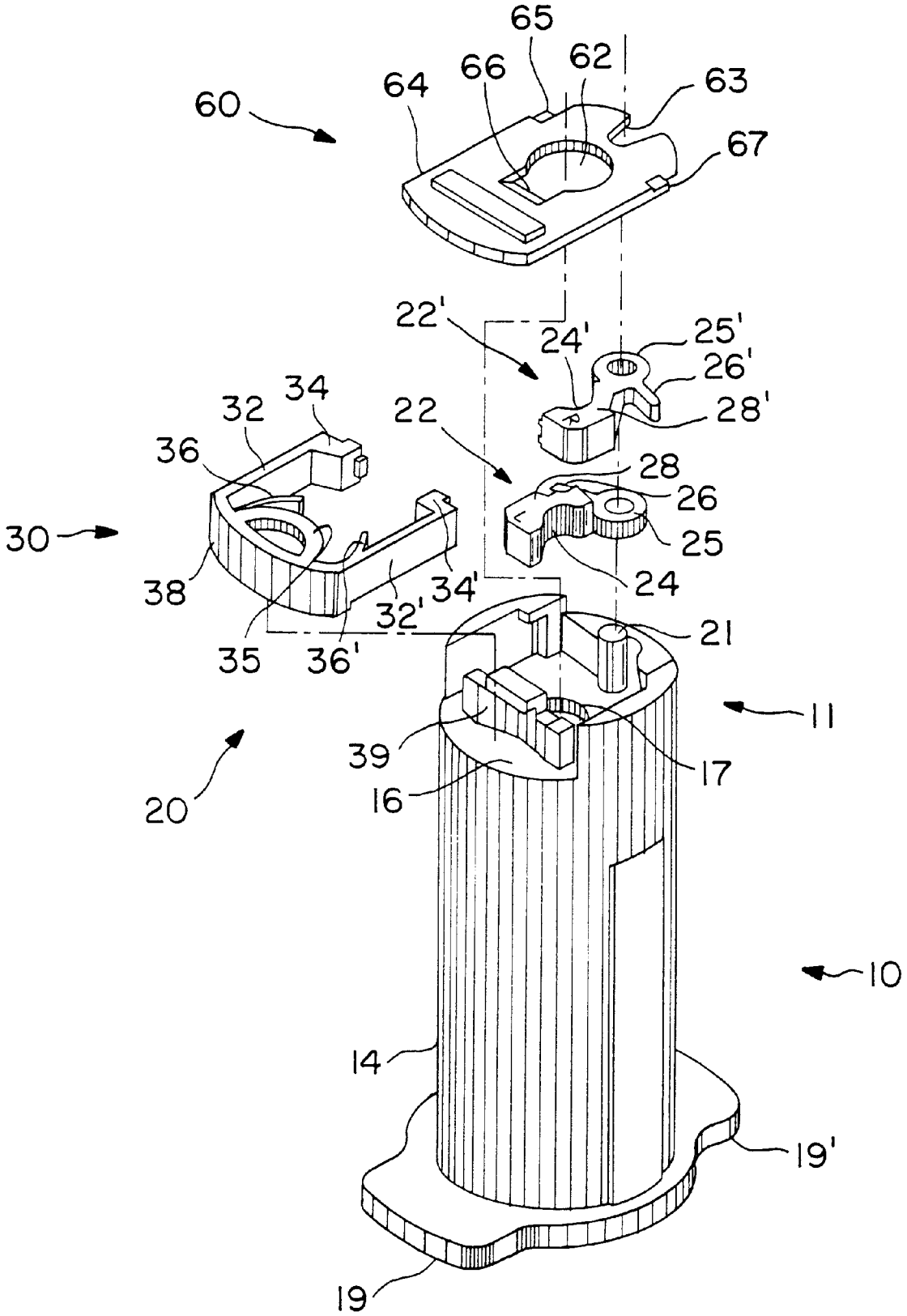
FIG. 2 is an exploded perspective view of the holder shown in FIG. 1.

With primary reference now to FIG. 2, the various components of holder 10 will be described in greater detail. As shown in FIG. 2, actuation mechanism 20 generally consists of a spring biased actuator, indicated generally at 30, a pivot axle 21 and first and second threaded halves 22 and 22', respectively. Housing 11 includes a bearing wall 39, the end cap 60, sidewalls 18 and 18' and end walls 15 and 15' (see FIGS. 3a and 3b). While bearing wall 39 and pivot axle 21 are preferably integrally formed with an end wall 16 of hollow body 14, threaded halves 22 and 22', and actuator 30, are movably mounted to housing 11. Actuation mechanism 20 is captured within housing 11 between end wall 16 and end cap 60. As shown in FIG. 2, threaded halves 22 and 22' preferably include apertured collars 25 and 25' which are pivotably mounted within housing 11 via engagement with pivot axle 21. Alternatively, each of threaded halves 22 and 22' can be pivotably mounted within housing 11 for rotation about separate pivot axles. Threaded halves 22 and 22' also include first and second threaded surfaces 24 and 24', respectively, which generally face one another and which cooperate to define a threaded passageway 23 (see FIG. 3a) having a substantially circular cross-section when biased to the position shown in FIGS. 3a and 4a. First and second threaded halves 22 and 22' further include substantially planar first and second top surfaces 28 and 28', respectively, located substantially perpendicularly to threaded surfaces 24 and 24'. First and second torque members 26 and 26' extend from collars 25 and 25', respectively, and define torque arms for driving threaded halves 22 and 22' in respective first directions about pivot axle 21. Actuator 30 is generally in the form of a user-operable push-button which is operably associated with first and second threaded halves 22 and 22'. Actuator 30 generally consists of an external element 38, first and second driver arms 32 and 32' extending therefrom, resilient fingers 36 and 36', and a stop member 35. Additionally, drive projections 34 and 34', respectively, extend from the free ends of arms 32 and 32' for engagement with respective torque members 26 and 26'.

As shown in FIG. 2, substantially planar end cap 60 has an extended portion 64 at one end thereof, a recess 63 at an opposite end thereof, and an aperture 62 therebetween. Upon assembly of holder 10, end cap 60 serves to retain most of actuator 30 and first and second threaded halves 22 and 22' within housing 11. To secure end cap 60 to holder 10, end cap 60 preferably engages sidewalls 18 and 18' of housing 11 at beveled regions 65 and 67 and a lip on bearing wall 39 at a beveled region 66. Additionally, recess 63 of end cap 60 preferably engages pivot axle 21 in snap-fit fashion to prevent end cap 60 from sliding from holder 10. As an alternative, end cap 60 may be secured to holder 10 with many other well known fixation means such as adhesive bonding, affixation with fasteners or any equivalent thereof. When holder 10 is assembled, aperture 62 of end cap 60, aperture 17 of end wall 16 and threaded passageway 23 defined between threaded surfaces 24 and 24' are generally coaxial. This relationship defines a continuous passageway through which a threaded cannula 40 may pass upon insertion thereof into holder 10.

Figure 3B:
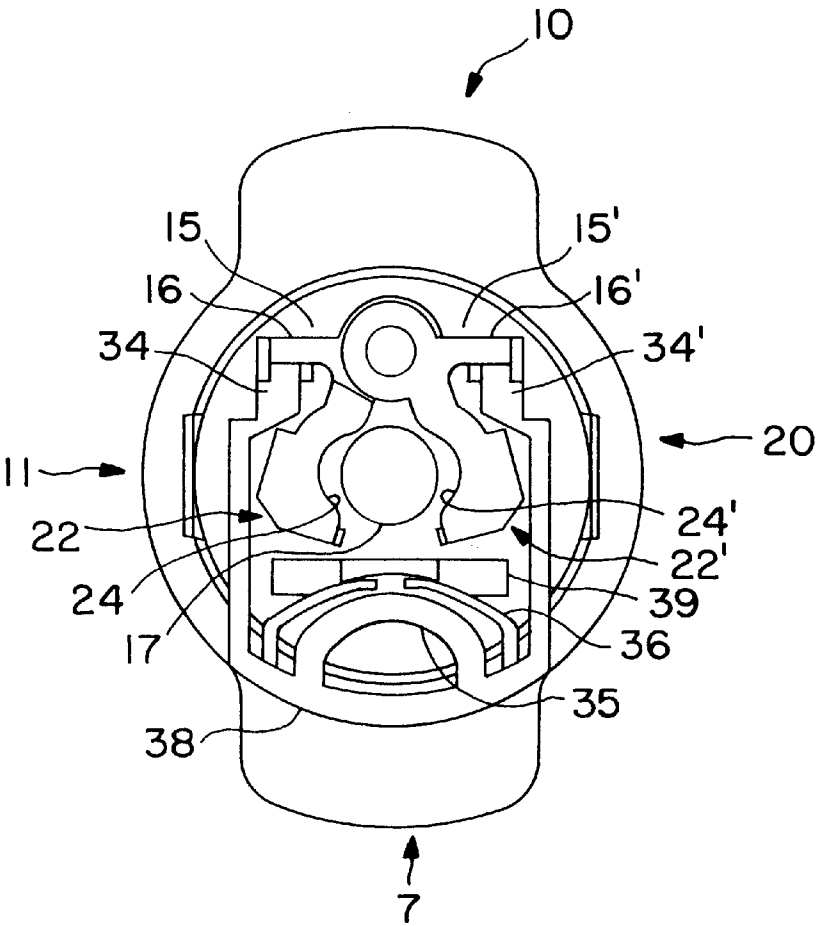
FIG. 3b is a view similar to FIG. 3a, illustrating the actuation mechanism in the retracted position.
Figure 3A:
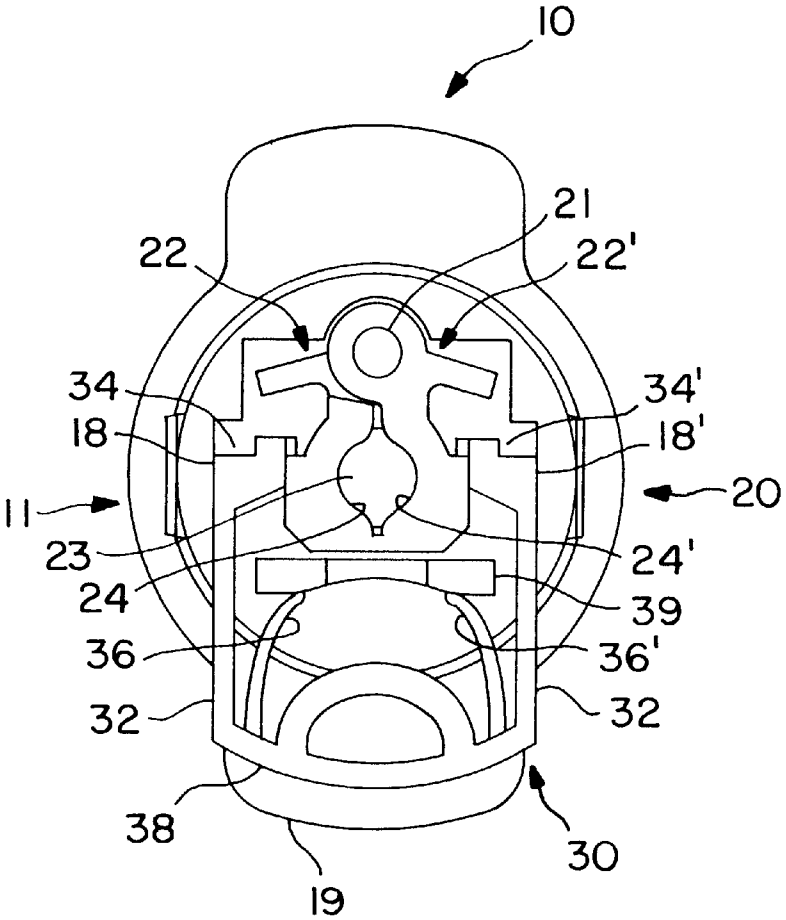
FIG. 3a is a cross-sectional view of the holder shown in FIGS. 1 and 2, illustrating the actuation mechanism in a cannula-mounting position.

The operation of the various components of actuation mechanism 20 will now be described with joint reference to FIGS. 3a and 3b. FIG. 3a shows a cross sectional view of the holder of FIGS. 1 and 2 illustrating actuation mechanism 20 in the cannula-mounting position. When actuation mechanism 20 is in this position, actuator 30 is urged radially outward with respect to housing 11 by the cooperation of resilient fingers 36 and 36' and bearing wall 39. In this position of actuator 30, external portion 38 thereof is substantially aligned with grip tab 19 and (FIG. 2) extended portion 64 of end cap 60. Furthermore, shoulders on drive projections 34 and 34' contact exterior surfaces of threaded halves 22 and 22' and arms 32 and 32', respectively, contact side walls 18 and 18' of housing 11 to constrain threaded halves 22 and 22' from pivoting apart. Thus, in the cannula-mounting position, cooperation between drive projections 34 and 34' and threaded halves 22 and 22', ensures maintenance of a rigid threaded passageway 23 between facing threaded surfaces 24 and 24'.

The movement of actuation mechanism 20 from the cannula-mounting position into the retracted position occurs upon user-operation of actuator 30. As described above, external element 38 of actuator 30 extends radially outwardly from holder 10 when actuation mechanism 20 is in the cannula-mounting position. Upon depression of external element 38 of actuator 30 in the direction of arrow 7 (see FIG. 3b), arms 32 and 32' cooperate with side walls 18 and 18' to guide actuator 30 linearly in the direction of arrow 7. Upon partial depression of external element 38, drive projections 34 and 34' temporarily disengage from threaded halves 22 and 22'. Thus, threaded halves 22 and 22' are no longer constrained from rotation about pivot axle 21. Upon further depression of external element 38, drive projections 34 and 34' engage torque members 26 and 26' to urge threaded halves 22 and 22' to pivot in opposite directions about pivot axle 21 from the cannula-mounting position to the retracted position shown in FIG. 3b. Simultaneously with depression of external element 38, resilient fingers 36 and 36' are bent inwardly and the outer surface of external element 38 becomes generally flush with the outer surface of holder 10. When actuator 30 is fully depressed, torque members 26 and 26' are pinched between end walls 15 and 15' of housing 11 and drive projections 34 and 34' of actuator 30. Additionally, resilient fingers 36 and 36' are pinched between bearing wall 39 and stop member 35 of actuator 30. Upon release of actuator 30, resilient fingers 36 and 36' and bearing wall 39 cooperate to urge actuator 30 to slide back to its initial position along a linear path in a direction opposite to that of arrow 7. During return of actuator 30 to its initial position, drive projections 34 and 34', once again, cooperate with threaded halves 22 and 22' to return threaded halves 22 and 22' to the cannula-mounting position. Optionally, a number of operationally equivalent structures can be used to pivot threaded halves 22 and 22' between the cannula-mounting and retracted positions. For example, at least one of torque members 26 and 26' can be positioned on top surfaces 28 and 28' of threaded halves 22 and 22', for engagement with at least one camming channel on actuator 30. An additional option includes providing threaded engagement between the various components of the actuation mechanism 20 such as between torque members 26 and 26' and actuator 30.

The cooperation between actuation mechanism 20 and threaded cannula 40 will now be described in greater detail with reference to FIGS. 4a and 4b. FIG. 4a depicts a cross-sectional view of holder 10 illustrating actuation mechanism 20 in the cannula-mounting position in combination with cannula 40. As shown therein, when threaded cannula 40 has been fully threaded into threaded passageway 23 of holder 10, threads 48 of cannula hub 45 engage threaded surfaces 24 and 24' of threaded halves 22 and 22'. Additionally, hub disk 46 of cannula hub 45 abuts top surfaces 28 and 28' to prevent further rotation of cannula 40. Since aperture 62 of end cap 60 and aperture 17 of end wall 16 are both appreciably larger than threaded passageway 23, the only contact between holder 10 and cannula 40 occurs between threads 48 and threaded surfaces 24 and 24', and between hub disk 46 and top surfaces 28 and 28'. Limiting contact between holder 10 and cannula 40 in this way helps ensure effective removal of cannula 40 from actuation mechanism 20 upon retraction of threaded halves 22 and 22'.

Figure 4B:
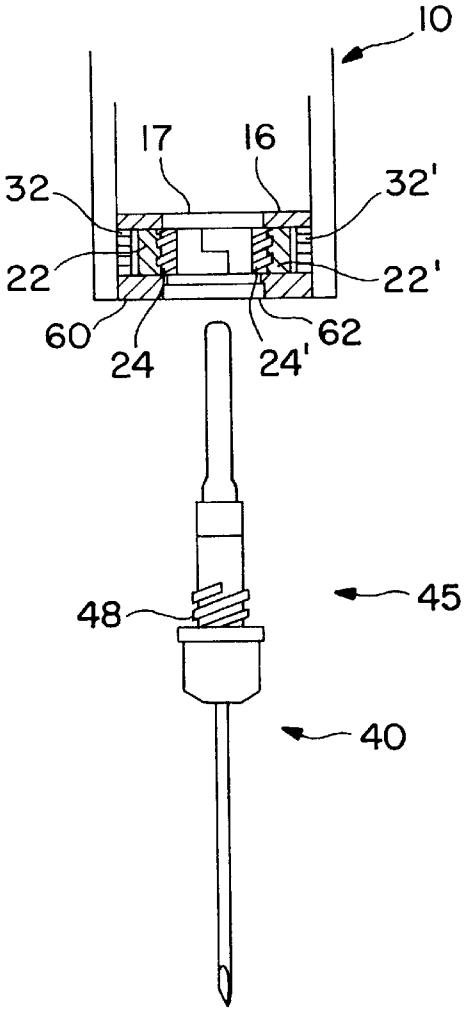
FIG. 4b is a fragmentary, medial sectional view, taken along the longitudinal axis, of the holder of FIGS. 1 and 2 shown in combination with a cannula.
Figure 4A:
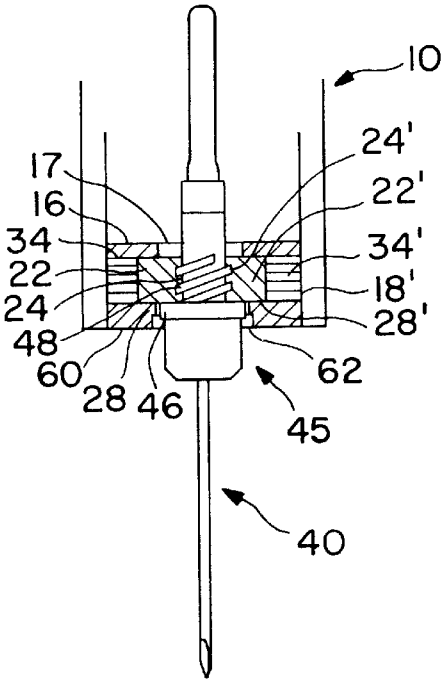
FIG. 4a is a fragmentary medial sectional view, taken along the longitudinal axis, of the holder of FIGS. 1 and 2 shown in combination with a cannula.

Referring now to FIG. 4b, actuation mechanism 20 is shown therein with threaded halves 22 and 22' in the retracted position and threaded cannula 40 aligned with, but detached from, actuation mechanism 20. As illustrated in FIG. 4b, the substantially thinner driver arms 32 and 32' of actuator 30 are generally aligned with threaded halves 22 and 22' to allow threaded halves 22 and 22' to retract away from one another. Also as shown, when threaded halves 22 and 22' are in the retracted position, threaded surfaces 24 and 24' no longer define a threaded passageway. Since threaded surfaces 24 and 24' are now generally aligned with the perimeters of apertures 62 and 17, threaded cannula 40 is detached from actuation mechanism 20. Thus, if holder 10 is oriented vertically, cannula 40 is free to fall from holder 10 under the force of gravity and holder 10 can be subsequently reused. The various components of holder 10 can be made from a wide variety of materials. In one reduction to practice, hollow body 14, housing 11, bearing wall 39 and pivot axle 21 are integrally formed from inexpensive, moldable plastic. Additionally, in this embodiment first and second threaded halves 22 and 22' and end cap 60 are also individually formed of inexpensive plastic. The actuator 30, however, is preferably made from an acetal, or equivalents thereof, because of its resilience, its durability and its low coefficient of friction. These properties enable resilient fingers 36 and 36' to provide sufficient biasing force against movement of actuator 30 while still allowing actuator 30 to freely glide against sidewalls 18 and 18' when depressed.

While a preferred embodiment of the present invention has been illustrated and described in detail, it should be readily appreciated that many modifications and changes thereto are within the ability of those of ordinary skill in the art. Therefore, the appended claims are intended to cover any and all of such modifications which fall within the true spirit and scope of the invention.

What is claimed is:

1. A needle holder for use with a fluid collection and/or injection system of the type having a double-ended cannula and a fluid container, the cannula including a fluid passage bore extending therethrough and a generally cylindrical, externally threaded hub with a hub disk at one end thereof, the fluid container including a sealed open end and an opposing closed end, said needle holder comprising:

a hollow body having an end wall at a closed first end thereof, said end wall having an aperture therethrough, said hollow body also having an open second end disposed opposite to said first end for receiving a fluid container within said hollow body such that, upon reception of the fluid container, the open end of the fluid container is adjacent to said end wall;

housing means abutting said first end of said hollow body for maintaining at least a portion of an actuation mechanism within said holder, said housing means including means defining an aperture therethrough which is generally coaxial with said aperture of said end wall; and an actuation mechanism for threadably mounting a threaded cannula hub therein with one end of the cannula extending forwardly of said actuation mechanism for venipuncture and the other end extending rearwardly into said hollow body for engagement with the fluid container, said actuation mechanism including:

first and second threaded halves mounted within said housing means for removably mounting the cannula hub upon threading the cannula hub into said actuation mechanism, each of said threaded halves including a threaded surface, at least one of said first and second threaded halves being movable between a cannula-mounting position wherein said threaded surfaces cooperate to define a threaded passageway complementary in cross-sectional shape to the cross-sectional shape of the threaded cannula hub, and a retracted position wherein said threaded surfaces cooperate to define an opening having a cross-sectional size which is greater than the cross-sectional size of the threaded cannula hub;

means for movably mounting at least one of said first and second threaded halves within said housing means; and actuation means for urging at least one of said first and second threaded halves between said cannula-mounting and retracted positions, said actuation means being slidably mounted to said housing means for movement between an initial position wherein at least one of said first and second threaded halves is urged into said cannula-mounting position, and a secondary position wherein at least one of said first and second threaded halves is urged into said retracted position.

2. The needle holder of claim 1 wherein said at least one of said first and second threaded halves is pivotable between the cannula-mounting position and the retracted position, and said means for movably mounting at least one of said first and second threaded halves within said housing means comprises means for pivotably mounting said at least one of said first and second threaded halves.

3. The needle holder of claim 2, wherein at least one of said first and second threaded halves further comprises a torque member; and wherein said actuation means includes:

a user-operable external element; and at least one drive arm extending from said actuation means, said drive arms engaging said torque members to urge at least one of said first and second threaded halves into said retracted position in response to the application of linear force to said user-operable external element.

4. The needle holder of claim 1 or claim 3, wherein said actuation means further comprises:

resilient means for biasing said actuation means to said initial position wherein at least one of said first and second threaded halves is urged into said cannula-mounting position by said drive arms of said actuation means.

5. The needle holder of claim 4, wherein said housing means further comprises:

a bearing wall for opposing said resilient means of said actuation means; and an end cap at one end of said holder for maintaining at least a portion of said actuation mechanism within said housing means, wherein said end cap includes said means defining an aperture in said housing means.

6. The needle holder of claim 5, wherein said end cap of said housing means is substantially planar and is slidably received in said housing means in snap-fit fashion.

7. The needle holder of claim 6, wherein said end cap of said housing means includes an extended portion which is substantially congruent with said external element of said actuation means when said actuation means is in said initial position.

8. The needle holder of claim 7, wherein each of said first and second threaded halves includes a top surface adjacent to said end cap of said housing means, and wherein engagement between said top surfaces of said threaded halves and the hub disk of the cannula hub limits further insertion of the cannula hub into said holder.

9. The needle holder of claim 1 or claim 2, wherein the diameter of said threaded passageway defined by said first and second threaded surfaces is smaller than the diameters of both of said apertures in said end cap and said end wall, and wherein the perimeter of said threaded passageway does not subtend the perimeters of either of said apertures of said end cap and of said end wall when said threaded halves are in said cannula-mounting position.

10. The needle holder of claim 5, wherein the diameter of said threaded passageway defined by said first and second threaded surfaces is smaller than the diameters of both of said apertures in said end cap and said end wall, and wherein the perimeter of said threaded passageway does not subtend the perimeters of either of said apertures of said end cap and of said end wall when said threaded halves are in said cannula-mounting position.

11. A needle holder for use with a fluid collection and/or injection system of the type having a needle assembly and a fluid container, the needle assembly including a fluid passage bore extending therethrough and a hub, the fluid container including a fluid passage end and an opposing end, said needle holder comprising:

a hollow body having an end wall at a closed first end thereof, said end wall having an aperture therethrough, said hollow body also having an open second end opposite to said first end for receiving a fluid container within said hollow body such that, upon reception of the fluid container, the fluid passage end of the fluid container is adjacent to said end wall;

housing means abutting said first end of said hollow body for maintaining at least a portion of an actuation mechanism within said holder, said housing means including means defining an aperture therethrough which is generally coaxial with said aperture of said end wall; and an actuation mechanism for detachably mounting a cannula hub therein with one end of the cannula extending forwardly of said actuation mechanism for venipuncture and the other end extending rearwardly into said hollow body for engagement with the fluid container, said actuation mechanism including:

first and second mounting jaws rotatably mounted within said housing means for removably mounting the cannula hub upon inserting the cannula hub into said actuation mechanism, said first and second mounting jaws being pivotable between a cannula-mounting position wherein said mounting jaws cooperate to define a passageway complementary in cross-sectional shape to the cross-sectional shape of the cannula hub, and a retracted position wherein said mounting jaws cooperate to define an opening having a cross-sectional size which is greater than the cross-sectional size of the cannula hub;

a pivot axle for rotatably mounting said first and second mounting jaws within said housing means; and actuation means for urging said first and second mounting jaws between said cannula-mounting and retracted positions, said actuation means being slidably mounted to said housing means for linear reciprocal movement between an initial position wherein said first and second mounting jaws are urged into said cannula-mounting position, and a secondary position wherein said first and second mounting jaws are urged into said retracted position.

12. The needle holder of claim 11 wherein said first and second mounting jaws comprise first and second threaded halves.

13. The needle holder of claim 11 or claim 12, wherein each of said first and second mounting jaws further comprises a torque member; and wherein said actuation means comprises:

a user-operable external element; and first and second arms extending from said external element, said first and second arms engaging respective torque members to urge said first and second mounting jaws into said retracted position in response to the application of linear force to said user-operable external element.

14. The needle holder of claim 13, wherein said actuation means further comprises:

resilient means for biasing said actuation means to said initial position wherein said first and second mounting jaws are urged into said cannula-mounting position by said first and second arms of said actuation means.

15. The needle holder of claim 14, wherein said housing means further comprises:

a bearing wall for opposing said resilient means of said actuator; and an end cap at one end of said holder for retaining at least a portion of said actuation mechanism within said housing means, wherein said end cap includes said means defining an aperture in said housing means.

16. The needle holder of claim 15, wherein said end cap of said housing means is substantially planar and is slidably received in said housing means in snap-fit fashion.

17. The needle holder of claim 16, wherein said end cap of said housing means includes an extended portion which is substantially congruent with said external element of said actuation means when said actuation means is in said initial position.

18. The needle holder of claim 17, wherein each of said first and second mounting jaws includes a top surface adjacent to said end cap of said housing means, and wherein engagement between said top surfaces of said mounting jaws and a hub disk of the cannula hub limits insertion of the cannula hub into said holder.

19. The needle holder of claim 11 or claim 12, wherein the diameter of said passageway defined by said first and second mounting jaws is smaller than the diameters of both of said apertures in said end cap and said end wall, and wherein the perimeter of said passageway does not subtend the perimeters of either of said apertures of said end cap and of said end wall when said mounting jaws are in said cannula-mounting position.

20. The needle holder of claim 15, wherein the diameter of said passageway defined by said first and second mounting jaws is smaller than the diameters of both of said apertures in said end cap and said end wall, and wherein the perimeter of said passageway does not subtend the perimeters of either of said apertures of said end cap and of said end wall when said mounting jaws are in said cannula-mounting position.

*21. A holder for removably mounting an externally threaded needle assembly, said holder comprising:*

*a hollow body having an open proximal end and a distal end closed by an end wall having an aperture therethrough;*

*first and second threaded jaws mounted at the end wall; and*

*an actuator assembly disposed at said distal end and comprising an actuator slidably mounted to said holder and operatively associated with at least one of said threaded jaws to move said at least one of said threaded jaws between a needle assembly mounting position in which said first and second threaded jaws cooperate to define a threaded passageway aligned with said aperture for receiving and securing such externally threaded needle assembly, and a needle assembly release position in which said passageway is sufficiently enlarged to free such externally threaded needle assembly from said holder.*

*22. A holder for removably mounting an externally threaded needle assembly, said holder comprising:*

*a hollow body having an open proximal end and a distal end closed by an end wall having an aperture therethrough;*

*first and second threaded jaws mounted at the end wall; and*

*an actuator slidably mounted to said holder at said distal end and operatively associated with at least one of said threaded jaws to move said at least one of said threaded jaws between a needle assembly mounting position in which said first and second jaws cooperate to define therebetween a threaded passageway having a first cross-sectional area and aligned with said aperture, and a needle assembly release position in which the threaded passageway has a second cross-sectional area which is larger than the first cross-sectional area.*

*23. The holder of claim 21 or claim 22 wherein said actuator is integral with at least one of said threaded jaws.*

*24. The holder of claim 21 or claim 22 wherein said needle assembly comprises a double-ended cannula.*

*25. The holder of claim 24 further comprising an evacuated container having a puncturable membrane which is penetrated by one end of said double-ended cannula.*

*26. The holder of claim 21 or claim 22 wherein at least one of said threaded jaws is slidable towards the other to position said jaws in the mounting position, and is slidable away from the other to position said jaws in the release position.*

*27. The holder of claim 21 or claim 22 wherein at least one of said threaded jaws is dimensioned and configured to move slidably in a single plane between the needle assembly mounted position and the needle assembly release position.*

*28. The holder of claim 27 wherein said actuator is dimensioned and configured to slidably move in a single plane.*

*29. The holder of claim 21 or claim 22 wherein said actuator is dimensioned and configured to slidably move in a single plane.*

*30. A method for mounting an externally threaded needle assembly to a holder and thereafter releasing the needle assembly therefrom, the holder having a distal end at which is disposed an actuator and first and second threaded jaws, at least one of which jaws is movable relative to the other, the first and second threaded jaws cooperating to form therebetween a threaded passageway, and the actuator being operatively associated with at least one of threaded jaws, the method comprising the steps of:*

*securing a needle assembly into the threaded passageway;*

*thereafter operating the actuator to slide at least one of the threaded jaws in a single plane away from the other threaded jaw to thereby sufficiently enlarge the threaded passageway to release the needle assembly from said holder.*

*31. The method of claim 30 including operating the actuator by sliding it in the single plane.*

*32. The method of claim 30 or claim 31 wherein the step of securing a needle assembly into the threaded passageway is carried out by operating the actuator to slide at least one of the threaded jaws away from the other threaded jaw to thereby sufficiently enlarge the threaded passageway to position the needle assembly therewithin, and then operating the actuator to slide at least one of the threaded jaws towards the other threaded jaw to engage the needle assembly within the passageway.*

* * * * *